United States Patent [19]

Belous et al.

[11] 4,093,665
[45] June 6, 1978

[54] ARYL PERFLUORO-ALKYL ETHERS AND METHOD OF PRODUCING THEM

[76] Inventors: Viktor Mikhailovich Belous, ulitsa Ujutnaya, 5-a, kv. 3., Odessa; Lev Moiseevich Yagupolsky, ulitsa Ivana Kudri, 41, kv. 48., Kiev; Ljubov Antonovna Alexeeva, Proletarsky bulvar, 41, kv. 28., Odessa; Sergei Vasilievich Sokolov, ulitsa 3 Internatsionala, 67, kv. 222.; Alexei Ivanovich Ponomarev, ulitsa Ziny Portnovoi, 21, Korpus 1, kv. 18., both of Leningrad, all of U.S.S.R.

[21] Appl. No.: 728,598

[22] Filed: Sep. 29, 1976

Related U.S. Application Data

[63] Continuation of Ser. No. 628,237, Nov. 3, 1975, abandoned.

[30] Foreign Application Priority Data

Nov. 1, 1974   U.S.S.R. ............................... 2071094

[51] Int. Cl.$^2$ ..................... C07C 43/28; C07C 41/00
[52] U.S. Cl. ........................... 260/612 D; 260/613 D; 106/33
[58] Field of Search .................. 260/612 D, 613 D

[56] References Cited
PUBLICATIONS
Sheppard, JACS vol. 83, (1961), 4860–4861.

*Primary Examiner*—Bernard Helfin
*Attorney, Agent, or Firm*—Haseltine, Lake & Waters

[57] ABSTRACT

The present invention relates to aryl perfluoro-alkyl ethers that are compounds of the general formula:

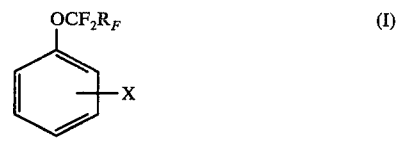

(I)

where
$R_F = CF_3$ or $CF_2OCF_3$, $X = Br$;
$R_F = CF_2OCF_3$, $X = NO_2$.

and also to a method of producing them. The method according to the present invention consists in fluorinating aryl esters of perfluorocarboxylic acids of the general formula

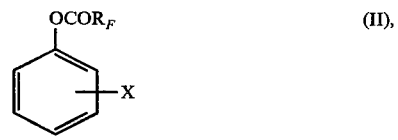

(II), where $R_F$ and X are as defined above, with sulphur tetrafluoride in autoclaves at a temperature of 20°–100° C in hydrogen fluoride solution with the concentration of the starting esters in hydrogen fluoride being 20–50%. Aryl perfluoroalkyl ethers can be used as intermediate products for producing medicinal preparations, heat-, cold-, benzene, and oil-resistant sealing compounds, as well as compounds and polymers applied in various fields of engineering. The above-described method allows obtaining the desired products under mild conditions with a high yield (80% of theory).

2 Claims, No Drawings

ARYL PERFLUORO-ALKYL ETHERS AND METHOD OF PRODUCING THEM

This is a continuation of U.S. Pat. application Ser. No. 628,237 filed Nov. 3, 1975 and now abandoned.

The present invention relates to novel compounds-aryl perfluoro-alkyl ethers and to a method of producing them.

According to the invention, aryl perfluoro-alkyl ethers are compounds of the general formula:

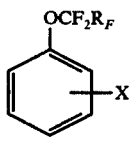

(I)

where $R_F = CF_3$ or $CF_2OCF_3$; $X = Br$;
$R_F = CF_2OCF_3$, $X = NO_2$.

Said compounds can be used as intermediate products for producing medicines, heat-, cold-, benzene- and oil-resistant sealing compounds, as well as compounds and polymers applied in various fields of engineering.

Said aryl perfluoro-alkyl ethers can be produced by a method which, according to the invention, consists in fluorinating aryl esters of perfluoro-carboxylic acids of the general formula:

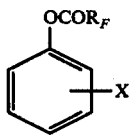

(II), where $R_F = CF_3$ or $CF_2OCF_3$, $X = Br$;
$R_F = CF_2OCF_3$, $X = NO_2$.

with sulphur tetrafluoride in autoclaves at a temperature of 20–100° C in hydrogen fluoride solution with the concentration of the starting esters in hydrogen fluoride being 20–50%.

The above-mentioned method is carried out under mild conditions (at a temperature of 20°–100° C). The method allows obtaining valuable aryl perfluoro-alkyl ethers, not available before, with a high yield (80% of theory).

As mentioned above, said aryl perfluoro-alkyl ethers are synthesized in an autoclave.

The required amounts of aryl ester of perfluoro-carboxylic acid, hydrogen fluoride and sulphur tetrafluoride are charged into an autoclave and maintained at the reaction temperature. When the process is completed, gaseous reaction products are allowed to escape, the reaction mixture is poured out into water, and the desired aryl perfluoro-alkyl ethers are distilled off with water vapours.

For a better understanding of the present invention given hereinbelow are examples illustrating specific embodiments of the proposed method.

EXAMPLE I 5.38 grams (0.02 mol) of m-bromo-phenyl ester of trifluoroacetic acid, 7 grams of hydrogen fluoride and 4 grams of sulphur tetrafluoride are heated to 100° C during 2 hours in a stainless steel autoclave of 70 ml capacity. Then the autoclave is cooled, and gaseous products are let out therefrom. The reaction mixture is carefully poured out into water and the resultant product is distilled off with water vapours; the distillate is extracted with diethyl ether. The ethereal solution is washed with water, then with 10% sodium hydroxide solution, again with water, and dried. Ether is distilled off, and the residue is vacuum-distilled.

The yield of m-bromo-phenyl-pentafluoro-ethyl ether is 4.37 grams (75.4% of theory).

Boiling point, 77°–79° C (30 mm Hg); $d_4^{25}$, 1.665; $n_D^{25}$, 1.4285.

Found: $MR_D$, 45.61. Calculated: $MR_D$, 45.96. Found, %: Br, 27.59; 27.68; F, 32.51; 32.50. $C_8H_4OBrF_5$. Calculated, %: Br, 27.47; F, 32.66.

EXAMPLE 2

In the above-described autoclave 5.38 grams (0.02 mol) of p-bromo-phenyl ester of trifluoro-acetic acid, 20 grams of hydrogen fluoride and 4 grams of sulphur tetrafluoride are heated to 50° C during 4 hours. The resulting product is treated in the same way as in Example I.

The yield of p-bromo-phenyl-pentafluoro-ethyl ether is 4.35 grams (75.1%).

Boiling point, 91°–93° C (50 mm Hg); $d_4^{25}$, 1.654, $n_D^{25}$, 1.4327. Found: $MR_D$, 45.60. Calculated: $MR_D$, 45.96. Found, %: Br, 27.59; 27.68; F, 32.39; 32.40. $C_8H_4OBrF_5$. Calculated, %: Br, 27.47; F, 32.66.

EXAMPLE 3

In the above-described autoclave 6.7 grams (0.02 mol) of m-bromo-phenyl ester of difluoro-(trifluoromethoxy)-acetic acid, 13 grams of hydrogen fluoride and 4 grams of sulphur tetrafluoride are heated to 100° C during 2 hours and the resulting product is isolated by following the procedure described in Example I.

The yield of m-bromo-phenyl-tetrafluoro-1-trifluoromethoxyethyl ether is 5.46 grams (76.5%).

Boiling point, 82°–85° C (20 mm Hg); $d_4^{20}$, 1.673; $n_D^{20}$, 1.4063. Found: $MR_D$, 52.43. Calculated: $MR_D$, 52.69. Found, %: Br, 22.01; 22.30; F, 37.44; 37.62. $C_9H_4O_2BrF_7$. Calculated, %: Br, 22.41; F, 37.25.

EXAMPLE 4.

In the same autoclave 6.02 grams (0.02 mol) of m-nitrophenyl ester of difluoro-(trifluoromethoxy)-acetic acid, 6 grams of hydrogen fluoride and 4 grams of sulfur tetrafluoride are heated to 50° C during 2 hours and kept during 12 hours at 20° C. The reaction products are treated by following the procedure described in Example I.

The yield of nitro-phenyl-tetrafluoro-2-trifluoromethoxy-ethyl ether is 5.4 grams (83.6%).

Boiling point, 88°–90° C (5 mm Hg); $n_D^{17}$, 1.4085. Found, %: F, 40.82; 40.95; N, 4.24; 4.32 $C_9H_4O_4F_7N$. Calculated, %: F, 41.17; N, 4.33.

What is claimed is:

1. Aryl perfluoro-alkyl ethers of the formula

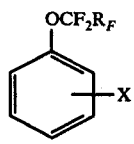

(I)

where $R_F = CF_3$ or $CF_2OCF_3$, $X = Br$;

$R_F = CF_2OCF_3$, $X = NO_2$

2. A method of producing aryl perfluoro-alkyl ethers of the formula

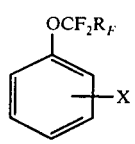

where
$R_F = CF_3$, $CF_2OCF_3$, $X = Br$;
$R_F = CF_2OCF_3$, $X = NO_2$, which comprises fluorinating of aryl esters of perfluorocarboxylic acids of the general formula

(II)

where $R_F$ and $X$ are as defined above, with sulphur tetrafluoride in an autoclave at a temperature of 25°–100° C in hydrogen fluoride solution with the concentration of the starting esters in hydrogen fluoride being 20–50%.

* * * * *